United States Patent
Roche et al.

(10) Patent No.: US 8,000,926 B2
(45) Date of Patent: Aug. 16, 2011

(54) METHOD AND SYSTEM FOR POSITIONAL MEASUREMENT USING ULTRASONIC SENSING

(75) Inventors: Martin Roche, Fort Lauderdale, FL (US); Marc Boillot, Plantation, FL (US); Jason McIntosh, Sugar Hill, GA (US)

(73) Assignee: Orthosensor, Sunrise, FL (US)

( * ) Notice: Subject to any disclaimer, the term of this patent is extended or adjusted under 35 U.S.C. 154(b) by 0 days.

(21) Appl. No.: 12/764,072

(22) Filed: Apr. 20, 2010

(65) Prior Publication Data

US 2010/0204955 A1 Aug. 12, 2010

Related U.S. Application Data

(63) Continuation-in-part of application No. 11/562,404, filed on Nov. 21, 2006, now Pat. No. 7,725,288.

(60) Provisional application No. 60/740,151, filed on Nov. 28, 2005, provisional application No. 61/291,725, filed on Dec. 31, 2009.

(51) Int. Cl.
*G01B 7/02* (2006.01)
(52) U.S. Cl. ............. 702/159; 702/72; 702/94; 702/150
(58) Field of Classification Search .................... 702/66, 702/72, 159
See application file for complete search history.

(56) References Cited

U.S. PATENT DOCUMENTS

| | | | | |
|---|---|---|---|---|
| 3,745,518 A | * | 7/1973 | Barret et al. ..................... 367/6 |
| 4,751,689 A | * | 6/1988 | Kobayashi ................... 367/127 |
| 4,807,202 A | * | 2/1989 | Cherri et al. .................. 367/129 |
| 5,280,457 A | * | 1/1994 | Figueroa et al. .............. 367/127 |
| 5,339,259 A | * | 8/1994 | Puma et al. ................... 702/153 |
| 5,504,477 A | * | 4/1996 | Whitright et al. ............ 340/10.4 |
| 6,090,114 A | | 7/2000 | Matsuno et al. |
| 6,546,277 B1 | | 4/2003 | Franck et al. |
| 7,139,418 B2 | | 11/2006 | Abovitz et al. |
| 7,309,339 B2 | | 12/2007 | Cusick et al. |
| 7,392,076 B2 | | 6/2008 | Moctezuma de La Barrera |
| 7,395,181 B2 | | 7/2008 | Foxlin |
| 7,477,926 B2 | | 1/2009 | McCombs |
| 7,559,931 B2 | | 7/2009 | Stone |
| 7,604,645 B2 | | 10/2009 | Barzell et al. |
| 7,636,595 B2 | | 12/2009 | Marquart et al. |
| 7,657,298 B2 | | 2/2010 | Moctezuma de la Barrera et al. |
| 7,660,623 B2 | | 2/2010 | Hunter et al. |

(Continued)

OTHER PUBLICATIONS

Wickline A., "Helping to Make Total Knee Replacement Even Better", St. Elizabeth Medical Center, Brochure, pg. 1-2. (non-dated) http://www.geneseeortho.com/pdfs/kneebroch.pdf.

(Continued)

*Primary Examiner* — Drew A Dunn
*Assistant Examiner* — Mi'schita' Henson
(74) *Attorney, Agent, or Firm* — Marc Boillot

(57) ABSTRACT

A method for determining position and alignment is provided. The method includes monitoring a first and second sequence of ultrasonic signals transmitted from the first device to a second device, estimating a location of the first device from Time of Flight measurements of the ultrasonic signals at respective microphones on the second device, calculating a set of phase differences, weighting a difference of an expected location and estimated location of the first device with the set of phase differences to produce a relative displacement, and reporting a position of the first device based on the relative displacement.

15 Claims, 5 Drawing Sheets

U.S. PATENT DOCUMENTS

| | | | |
|---|---|---|---|
| 7,681,448 | B1 | 3/2010 | Preston et al. |
| 7,685,861 | B2 | 3/2010 | Lynch et al. |
| 7,689,032 | B2 | 3/2010 | Strassenburg-Kleciak |
| 7,771,436 | B2 | 8/2010 | Moctezuma et al. |
| 7,824,328 | B2 | 11/2010 | Gattani et al. |
| 2001/0011175 | A1 | 8/2001 | Hunter et al. |
| 2004/0024309 | A1 | 2/2004 | Ferre et al. |
| 2004/0236424 | A1 | 11/2004 | Berez et al. |
| 2004/0254584 | A1 | 12/2004 | Sarin et al. |
| 2005/0197139 | A1* | 9/2005 | Misikangas et al. ....... 455/456.1 |
| 2006/0235420 | A1 | 10/2006 | Irving |
| 2007/0175489 | A1 | 8/2007 | Moctezuma et al. |
| 2008/0269599 | A1 | 10/2008 | Csavoy et al. |
| 2009/0318836 | A1 | 12/2009 | Stone et al. |
| 2010/0063508 | A1 | 3/2010 | Borja et al. |
| 2010/0069911 | A1 | 3/2010 | Borja et al. |
| 2010/0076505 | A1 | 3/2010 | Borja et al. |
| 2010/0137869 | A1 | 6/2010 | Borja et al. |
| 2010/0160771 | A1 | 6/2010 | Gielen et al. |
| 2010/0210939 | A1 | 8/2010 | Hartmann et al. |

OTHER PUBLICATIONS

Edwards, S.," Stryker Navigation System", Baystate Medical Center, Brochure, pp. 1-7. .(non-dated) http://www.baystatehealth.org/StaticFiles/Baystate/Services/Surgery/Surgery%20at%20BMC/Hip%20Knee%20Replacement/Computer-assisted%20Surgery/Stryker/Stryker.prf.

Kang. M, "Early Clinical Results Show High Degree of Accuracy and Ease-of-Use KneeAlign Surgical Navigation System", CAOS Meeting, Paris, France, Jun. 19, 2010. http://www.orthalign.com/corporate/news/2010/2010JUN21.asp.

"Computer Assisted Surgical Navigational Orthopedic Procedures", BlueCross BlueShield of North Carolina, Oct. 2004, Corporate Medical Policy. http://www.bcbsnc.com/assets/services/public/pdfs/medicalpolicy/computer_assisted_surgical_navigational_orthopedic_procedures.pdf.

"Computer-assisted Musculoskeletal Surgical Navigational Orthopedic Procedure". BlueCross BlueShield of Minnesotta, Medical and Behavioral Health Policy Manual, Medical and Behavioral Health Policy Manual. Effective Date: Feb. 9, 2011 http://notes.bluecrossmn.com/web/medpolman.nsf/50c3d5c81dd37e6a862569bd0054c1b2/f9c0a3e1697cd345862575bb007dea7d/$FILE/Computer-Assisted%20Musculoskeletal%20Surgical%20Navigational%20Orthopedic%20Procedure.pdf.

S. Parratte et. al., "Effect of Postoperative Mechanical Axis Alignment on the Fifteen-Year Survival of Modern, Cemented Total Knee Replacements " 2010 ;92:2143-9, Journal of Bone & Jiont Surgery http://www.sfha.com/usr/Deana%20Gladem/Postop%20Mechanical%20Axis%20Alignment,%20Cemented%20Knee.pdf.

"Medical Necessity Guidelines, Knee Arthroplasty", CareAllies, No. 0347, May 15, 2007, http://www.careallies.com/pdf/ex198_knee_arthroplasty.pdf.

F.W. Werner et. Al. "The effect of valgus/varus malalignment on load distribution in total knee replacements", Journal of Biomechanics 38 (2005) 349-355 http://www.engr.ku.edu/~kubiomech/ejbrl/PDF/JOURNALS/JB_38_2.pdf.

R. Nabeyama et al., "The accuracy of image-guided knee replacement based on computed tomography", 2004 ;86-B:366-71, Journal of Bone & Joint Surgery. http://web.jbjs.org.uk/cgi/content/abstract/86-B/3/336.

Mont, M.A., "Effect of postoperative Mechanical Axis Alignment . . ." Commentary & Perspective, Sep. 15, 2010, http://commentary.jbjs.org/index.php/2010/09/148.

Heck D.A., Computer Assisted Surgery (CAS), Baylor Health Care System, Slide Presentation, (non-dated) http://www.nist.gov/el/isd/upload/Computer_Assisted_Surgery_Heck.pdf.

* cited by examiner

METHOD AND SYSTEM FOR POSITIONAL MEASUREMENT USING ULTRASONIC SENSING

CROSS-REFERENCE TO RELATED APPLICATION

This application is a Continuation-In-Part of U.S. patent application Ser. No. 11/562,404 filed on Nov. 21, 2006 claiming the priority benefit of U.S. Provisional Patent Application No. 60/740,151 filed Nov. 28, 2005, the entire contents of which are hereby incorporated by reference. This application also claims priority benefit to Provisional Patent Application No. 61/291,725 filed Dec. 31, 2009, the entire contents of which are hereby incorporated by reference.

BACKGROUND

1. Field

The present embodiments of the invention generally relates to the field of motion sensing, and more particularly to input pointing devices.

2. Introduction

Motion detection systems can include radar systems, video camera monitoring systems, and medical diagnostic systems. Motion detection systems generally include a sensor which converts a physical signal into an electronic signal. The sensor performs the task of capturing the signal and converting it to a suitable format for processing. A motion detection system can include an input device for interpreting the sensory information and identifying whether an object has moved.

Such systems provide general proximity detection and movement tracking. A need however can arise for determining accurate position and alignment.

DETAILED DESCRIPTION

Figure 1:
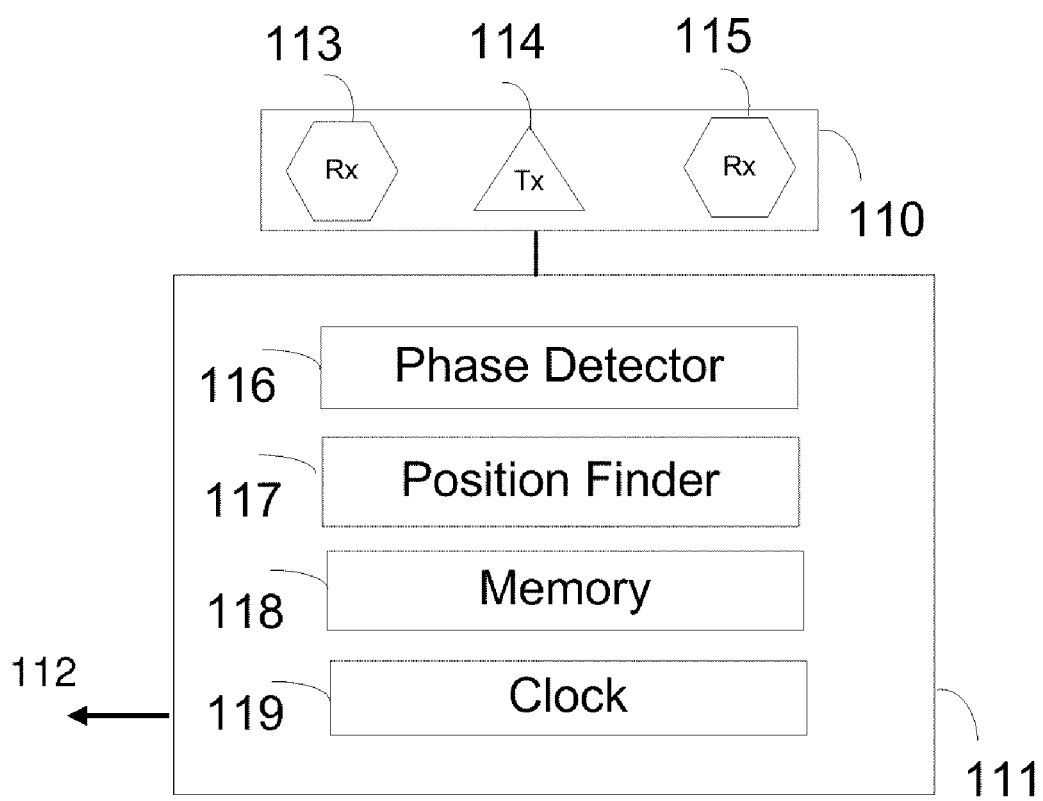
FIG. 1 is an ultrasonic device for tracking object movement and position in accordance with an embodiment of the inventive arrangements.

While the specification concludes with claims defining the features of the invention that are regarded as novel, it is believed that the invention will be better understood from a consideration of the following description in conjunction with the drawing figures, in which like reference numerals are carried forward.

Referring to FIG. 1, an ultrasonic device 100 is shown. The ultrasonic device 100 includes a sensing unit 110 for creating an ultrasonic sensing space, and a controller 111 for operating the sensing unit 110. The ultrasonic device 100 detects movement and location of an object in the ultrasonic sensing space 101. A display 112 can be coupled to the ultrasonic device 100 for showing the movement or position of the object. The sensing unit 110 can include an ultrasonic transmitter 114, a first receiver 113 and a second receiver 115 for sensors. The sensors can be ultrasonic transducers, acoustic microphones, Micro Electro Mechanical Element (MEMS) microphones, or other acoustic sensors for converting a physical media to an electric signal such as a voltage or current.

The sensors can be an array (e.g., line, rows, cols, etc.) or other arranged pattern (e.g., cross, triangle, circle, etc.) of sensing elements. As one example, the sensing element can be ultrasonic for transmitting and receiving ultrasonic signals. In another arrangement, the sensing element can be an array of microphones and speakers for transmitting and receiving ultrasonic and audio signals. In one arrangement, the ultrasonic device 100 can employ pulse-echo detection of reflected ultrasonic signals for determining its orientation with respect to an object within its proximity. The controller 111 can be an Application Specific Integrated Circuit (ASIC) or Field Programmable Gate Array (FPGA) or other fabricated electronic or analog component. In another arrangement, the sensing element can further include CCD camera elements or MEMS camera elements for processing light, and temperature sensors for monitoring temperature.

The ultrasonic device 100 can include, but is not limited to, a phase detector 116, a processor 117, a memory 118, and a clock 119. The sensing unit 110 can be integrated within the ultrasonic device 100, or apart from it. The phase detector 116 can be cooperatively connected to the sensing unit 110 for processing transmitted and received ultrasonic signals. The phase detector 116 can be coupled to the processor 117 for calculating phase differences among multiple receive signals. The processor 117 can process these phase differences for estimating a movement the object in the sensing space 101.

Figure 2A:
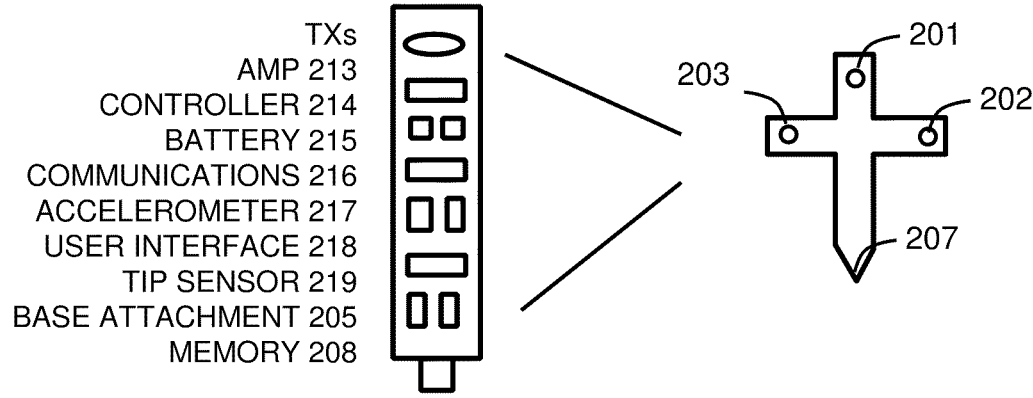
FIG. 2A is an ultrasonic transmit device for beaconing an orientation and position in accordance with an embodiment of the inventive arrangements.
Figure 2B:
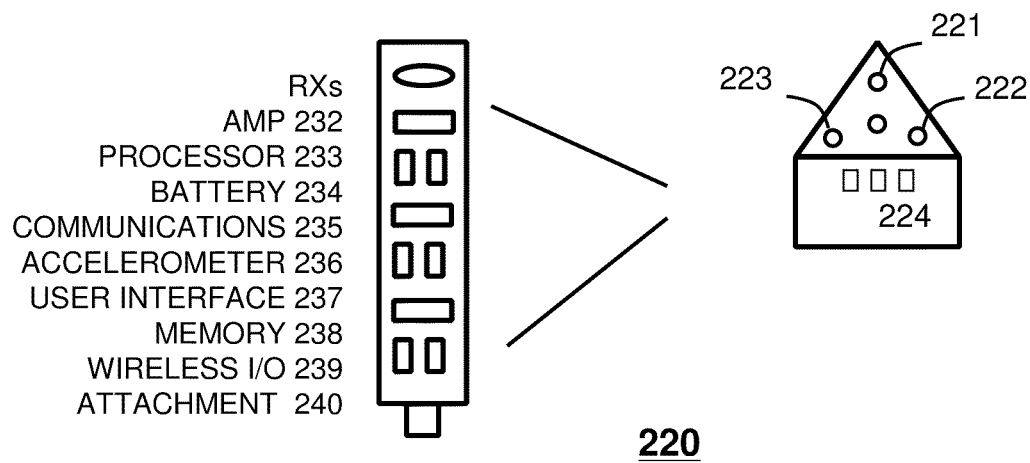
FIG. 2B is an ultrasonic receive device for locating a beaconing ultrasonic device in accordance with an embodiment of the inventive arrangements.

In one arrangement the ultrasonic device 100 can be partitioned out to a first device and a second device to separate the transmit operation from the receive operation. In this configuration, a system for positional measurement via ultrasonic tracking is provided. FIG. 2A illustrates one embodiment of a first device 200 with TXs (transmit sensors) 201-203 to provide transmit operation. FIG. 2B illustrates one embodiment of a second device 220 with RXs (receive sensors) 221-222 to provide receive operation.

The first device 200 shown in FIG. 2A comprises three ultrasonic transmitters 201-203 for each transmitting a first, second and third ultrasonic signals through the air, an electronic circuit (or controller) 214 for generating driver signals to the three ultrasonic transmitters 201-203 for generating the first, second and third ultrasonic signals, an user interface 218 that receives user input for performing short range positional measurement and alignment determination, a communications port 216 for relaying the user input and receiving timing information to control the electronic circuit 214, and a battery 215 for powering the electronic circuit 215 and associated electronics on the first device 200. The first device 200 may contain more or less than the number of components shown; certain component functionalities may be shared as integrated devices.

Additional ultrasonic sensors can be included to provide an over-determined system for three-dimensional sensing. The ultrasonic sensors can be MEMS microphones, ultrasonic receivers, ultrasonic transmitters or combination thereof. As one example, each ultrasonic transducer can perform separate transmit and receive functions. One example of an ultrasonic sensor is disclosed in U.S. patent application Ser. No. 11/683,410 entitled "Method and Device for Three-Dimensional Sensing" filed Mar. 7, 2007 the entire contents of which are hereby incorporated by reference. The ultrasonic sensor can transmit pulse shaped waveforms in accordance with physical characteristics of a customized transducer for constructing and shaping waveforms.

A tip 207 of the first device 200 indirectly identifies points of interest on a structure, for example, a rod, bone, instrument or jig in three-dimensional space. Although the tip is not equipped with ultrasonic transducers, its spatial location in three-dimensional space is established by the three ultrasonic transmitters 201-203 arranged at the cross ends. The symmetrical cross shape It can be held in the hand as a wand to identify via the tip 207, points of interest such as (anatomical) features on the structure, bone or jig. The tip 207 can be touch sensitive to registers points responsive to a physical action, for example, touching the tip to an anatomical or structural location. The tip can comprise a mechanical accelerometer or actuated spring assembly for such purpose. In another arrangement it includes a capacitive touch tip or electrostatic assembly for registering touch.

The user interface 218 can include one or more buttons to permit handheld operation and use (e.g., on/off/reset button) and illumination elements to provide visual feedback. The first device 200 may further include a haptic module with the user interface 218. As an example, the haptic module may change (increase/decrease) vibration to signal improper or proper operation. The first device 200 provides material to cover the transmitters 201-202 to be transparent to sound (e.g., ultrasound) and light (e.g., infrared) yet impervious to biological material such as water, blood or tissue. In one arrangement, a clear plastic membrane (or mesh) is stretched taught; it may vibrate under resonance with a transmitted frequency. The battery 215 can be charged via wireless energy charging (e.g., magnetic induction coils and super capacitors).

The first device 100 can include a base attachment mechanism 205 for coupling to a structure, bone or a jig. As one example, the mechanism can be a magnetic assembly with a fixed insert (e.g., square post head) to permit temporary detachment. As another example, it can be a magnetic ball and joint socket with latched increments. As yet another example, it can be a screw post to an orthopedic screw.

The first device 200 can further include an amplifier 213 and the accelerometer 217. The amplifier enhances the signal to noise ratio of transmitted or received signals. The accelerometer 217 identifies 3 and 6 axis tilt during motion and while stationary. The communications module 216 may include components (e.g., synchronous clocks, radio frequency 'RF' pulses, infrared 'IR' pulses, optical/acoustic pulse) for signaling to the second device 220 (FIG. 2B). The controller 214, can include a counter, a clock, or other analog or digital logic for controlling transmit and receive synchronization and sequencing of the sensor signals, accelerometer information, and other component data or status. The battery 215 powers the respective circuit logic and components.

The controller 214 can utilize computing technologies such as a microprocessor (μP) and/or digital signal processor (DSP) with associated storage memory 108 such a Flash, ROM, RAM, SRAM, DRAM or other like technologies for controlling operations of the aforementioned components of the device. The instructions may also reside, completely or at least partially, within other memory, and/or a processor during execution thereof by another processor or computer system. An Input/Output port permits portable exchange of information or data for example by way of Universal Serial Bus (USB). The electronic circuitry of the controller can comprise one or more Application Specific Integrated Circuit (ASIC) chips or Field Programmable Gate Arrays (FPGAs), for example, specific to a core signal processing algorithm.

The controller can be an embedded platform running one or more modules of an operating system (OS). In one arrangement, the storage memory may store one or more sets of instructions (e.g., software) embodying any one or more of the methodologies or functions described herein.

The second device 220 shown in FIG. 2B comprises a processor 233 for generating timing information, registering a pointing location of the first device 200 responsive to the user input, and determining short range positional measurement and alignment from three or more pointing locations of the first device 200 with respect to the second device 220. It includes a communications interface 235 for transmitting the timing information to the first device 200 that in response transmits the first, second and third ultrasonic signals. The ultrasonic signals can be pulse shaped signals generated from a combination of amplitude modulation, frequency modulation, and phase modulation. Three microphones 221-223 each receive the first, second and third pulse shaped signals transmitted through the air. The memory 238 stores the first, second and third ultrasonics signals and can produce a history of ultrasonic signals or processed signals. It can also store wand tip positions, for example, responsive to a user pressing the button to register a location. The wireless communication interface (Input/Output) 239 wirelessly conveys the positional information and the short range alignment of the three or more pointing locations to a remote system. The remote system can be a computer, laptop or mobile device that displays the positional information and alignment information in real-time as described ahead. The battery powers the processor 233 and associated electronics on the second device 220. The second device 200 may contain more or less than the number of components shown; certain component functionalities may be shared or therein integrated.

Additional ultrasonic sensors can be included to provide an over-determined system for three-dimensional sensing. The ultrasonic sensors can be MEMS microphones, ultrasonic receivers, ultrasonic transmitters or combination thereof. As one example, each ultrasonic transducer can perform separate transmit and receive functions. One example of an ultrasonic sensor is disclosed in U.S. patent application Ser. No. 11/683, 410 entitled "Method and Device for Three-Dimensional Sensing" the entire contents of which are hereby incorporated by reference. The second device 220 can also include an attachment mechanism 240 for coupling to bone or a jig. As one example, the mechanism 240 can be a magnetic assembly with a fixed insert (e.g., square post head) to permit temporary detachment. As another example, it can be a magnetic ball and joint socket with latched increments.

The second device 220 can further include an amplifier 232, the communications module 235, an accelerometer, and processor 233. The amplifier 232 enhances the signal to noise of transmitted or received signals. The processor 233 can include a controller, counter, a clock, and other analog or digital logic for controlling transmit and receive synchronization and sequencing of the sensor signals, accelerometer information, and other component data or status. The accelerometer 236 identifies axial tilt (e.g., 3/6 axis) during motion and while stationary. The battery 234 powers the respective circuit logic and components.

The communications module 235 can include components (e.g., synchronous clocks, radio frequency 'RF' pulses, infrared 'IR' pulses, optical/acoustic pulse) for local signaling (to wand 102). It can also include network and data components (e.g., Bluetooth, ZigBee, Wi-Fi, GPSK, FSK, USB, RS232, IR, etc.) for wireless communications with a remote device (e.g., laptop, computer, etc.). Although external communication via the network and data components is herein contemplate, it should be noted that the second device 220 can include a user interface 237 to permit standalone operation. As one example, it can include 3 LED lights 224 to show three or more Wand tip pointing location alignment status. The user interface 237 may also include a touch screen or other interface display with its own GUI for reporting positional information and alignment.

The processor 233 can utilize computing technologies such as a microprocessor (μP) and/or digital signal processor (DSP) with associated storage memory 108 such a Flash, ROM, RAM, SRAM, DRAM or other like technologies for controlling operations of the aforementioned components of the terminal device. The instructions may also reside, completely or at least partially, within other memory, and/or a processor during execution thereof by another processor or computer system. An Input/Output port permits portable exchange of information or data for example by way of Universal Serial Bus (USB). The electronic circuitry of the controller can comprise one or more Application Specific Integrated Circuit (ASIC) chips or Field Programmable Gate Arrays (FPGAs), for example, specific to a core signal processing algorithm or control logic. The processor can be an embedded platform running one or more modules of an operating system (OS). In one arrangement, the storage memory 238 may store one or more sets of instructions (e.g., software) embodying any one or more of the methodologies or functions described herein.

Figure 3A:
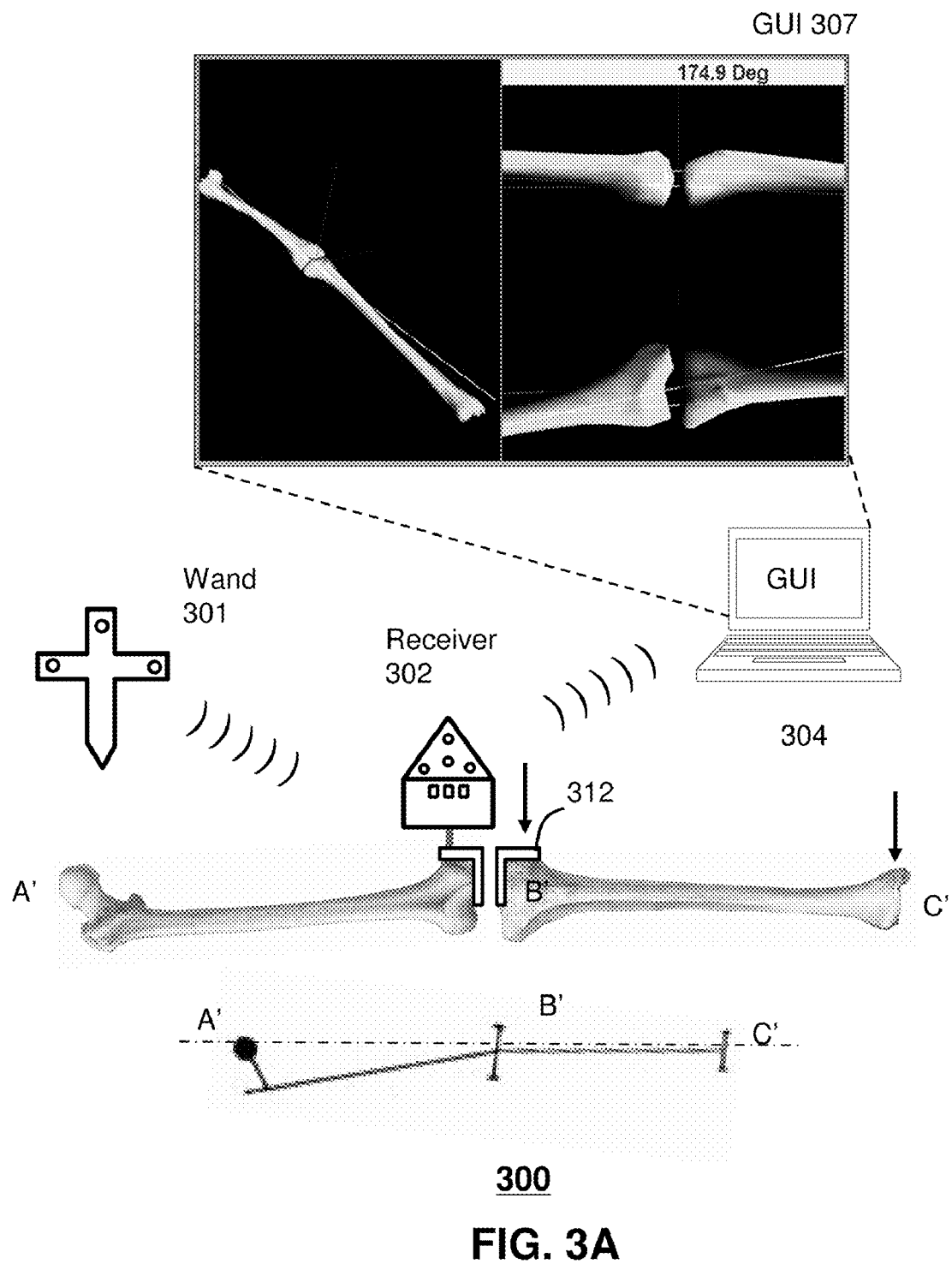
FIG. 3A is an exemplary ultrasonic system for reporting pointing location and alignment in accordance with one embodiment.

FIG. 3A depicts one exemplary embodiment of a system 300 using the first device 200 and second device 220 suitable for use as a positional measurement and alignment tool for orthopedic applications. The example illustrated is a system and method for intra-operatively assesses alignment of the femur and tibia bones.

The system 300 includes the hand-held portable ultrasonic device 301 (hereinafter Wand) and the optional mountable ultrasonic device 302 (hereinafter Receiver). The Wand 301 and Receiver 302 are low cost disposable components that can be delivered in a sterilized package. The Receiver 302 can communicate with the remote system 304 to report wand tip location, positional information and an orientation of the wand 301 in real-time. The Wand 301 and the Receiver 302 communicate directly with one another without outside reliance on a supervisory system; that is, the receiver 302 can determine the location and orientation of the Wand 301 within local view and with respect to its own coordinate system.

The Wand 301 is used to register points of interest in three-dimensional space with respect to the Receiver 302; points of interest can be spatial locations, for example, anatomical or structural locations on a bone or structure 312. The Wand 301 can also measure and report distance (e.g., mm, cm) between registered spatial points, for example, a gap distance between the distal femur and proximal tibia to determine a suitable sized insert. It can also be used to identify displacement, for example, an edge point or perimeter trace of an insert relative to its projected insertion location. The Wand 301 can also thereafter be affixed at these locations to report rotations and translations of the underlying object (e.g., bone, jig, insert, prosthetic etc) at these points, for example, relative to a reference orientation. This also permits for full range tracking and reporting of kinematic behavior. Such information can be used during the surgery to report range of joint motion and for comparison of post-surgical results.

In one embodiment, the system 300 comprises the Receiver 302 coupled to the jig 312, and the Wand 301 to register points of interest on a first and second bone with respect to the jig 312. The Receiver 302 and Wand 301 employ ultrasonic sensing and tracking to determine the Wands orientation and location relative to the Receiver 302 and the jig 312. Based on the registered points of interest, the Receiver 302 assesses and reports parameters related to the orientation of the jig 312 for aligning the first and second bone. The wand tip locations and orientations can also be stored for reference on the Receiver 302. Similarly, the system 300 can report alignment of the bones or jigs 312 by way of the Wand 301 and the Receiver 302 from these points of interest. The system 300 can assist in assessing alignment of the jigs 312 and bones for example, in knee replacement procedures. Software configurable parameters permit operation beyond the 3 m application range shown.

In one example, alignment is achieved when the points of the femur head (A'), knee center (B') and ankle (C') are positioned in a straight line as indicated by a positioning location of the Wand tip 301 at the second locations at separate times. Femur head identification of point (A') can be determined by affixing the Receiver 302 to the distal end of the femur and placing the Wand 301 at a stationary location in view (e.g., 1 m distance from Receiver 302). The femur is then rotated in a pattern for approximately 10-15 seconds to resolve the spherical center (femur head) as described in Provisional Patent Application No. 61/291,725 while the hip is sufficiently still. Upon establishing point (A'), the wand tip is then used to register the knee center (e.g., distal femur center) point B' when the leg is in flexion. Other anatomical locations can be registered fro providing further alignment information, for example, the proximal tibia. Thereafter, the wand tip is used to register the medial malleolus and the lateral malleolus which establishes the ankle center C' (e.g., eq: center=0.6*medial<x,y,z>)+0.4*lateral<x,y,z>).

Once these three (or more) points A', B' and C' are registered, the Wand 301 can be affixed midway on the tibia and in view of the Receiver 302. This permits real-time tracking of the tibia relative to the femur bone when the leg is in extension (straight) or in flexion (bent). In this fixed relationship, the Receive 302 can track a position and orientation of the Wand 301 relative to the Receiver's own coordinate system which inherently reveals any rotations and translations of the tibia relative to the femur (e.g., axial twist, left-right, up-down, forward-backward, and combinations thereof). As noted previously, this permits the system 300 to track and report a range of motion and associated kinematic information (e.g., axial twist, rotations, alignment) in accordance with a patient's expected orthopedic behavior during the procedure.

Certain aspects of alignment preparation can be performed before hand; for example, calibrating the Receiver 302 to the jig 312 or Wand 301. It can also transmit the positional information to associated wireless devices (e.g., laptop, cell phone, net book) like the remote system 304 and upload the information to a server on a network for example one connected to electronic medical or health care records. The system 300 can assess and report in real-time the position of these points for determining alignment, or other registered points, by way of a graphical user interface on the communication device 304.

Figure 3B:
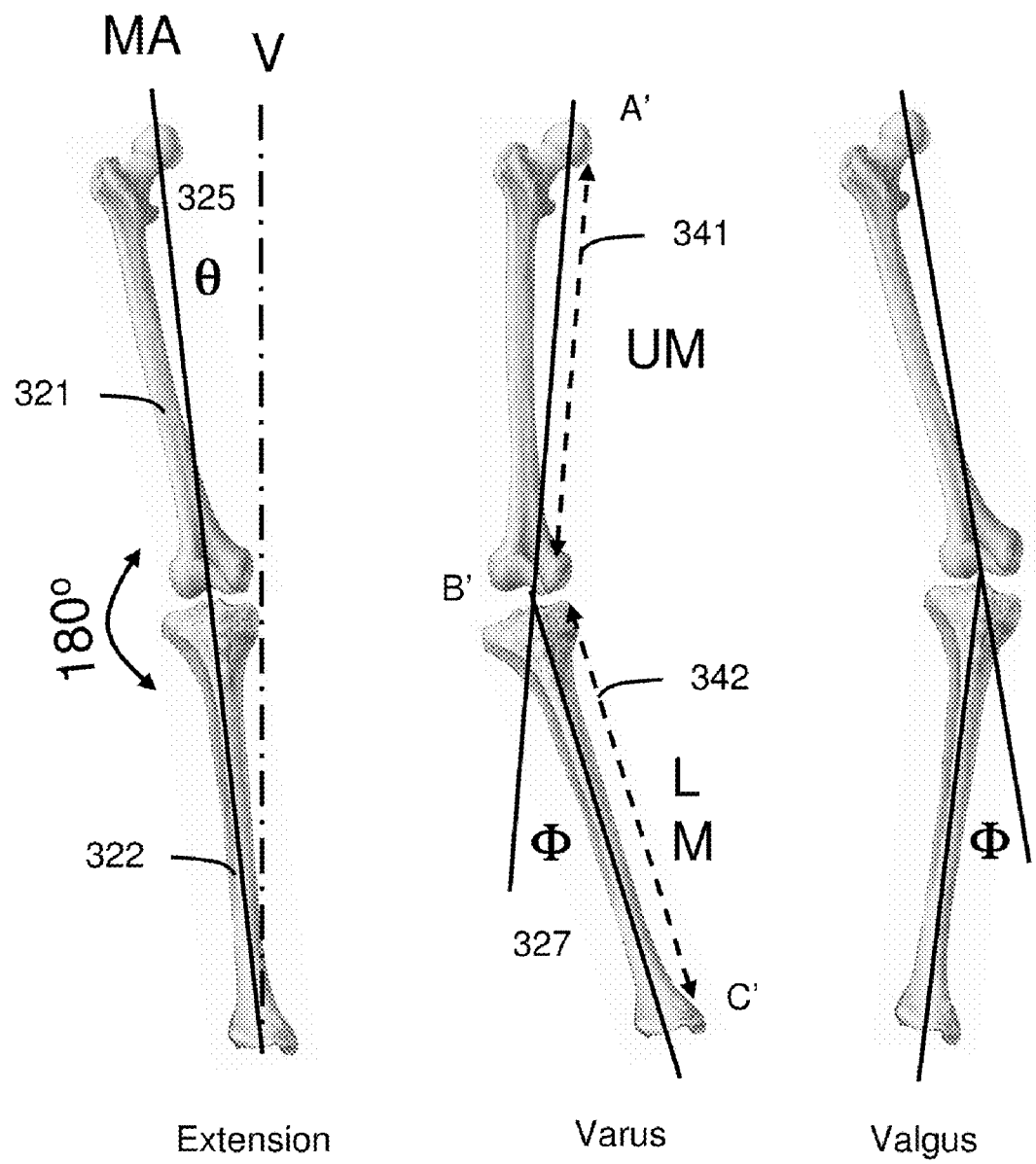
FIG. 3B is an illustration of anatomical deviations with respect to mechanical axis alignment.

FIG. 3B shows alignment along a mechanical axis of a leg for normal and abnormal conditions. In extension, the femur 321 and tibia 322 of the leg are aligned along the mechanical axis (MA). The MA is approximately θ~=6 degrees 325 from the vertical (V) at the ankle; and approximately 15-18 degrees from the vertical (V) at the knee (Q-angle) for a straight leg in standing position. As illustrated in the center subplot, a varus deformity is an outward angulation of the distal segment of a bone or joint with an alignment angle (or error) described by −Φ327. As illustrated in the right subplot a valgus deformity is a term for the inward angulation of the distal segment of a bone or joint with an alignment angle (or error) described by +Φ327.

The system 300 reports the alignment angle Φ327 between the first line 341 and the second line 342 as part of the positional location (information). The first line 341 is defined by the first point A' at a first time and a second point B' at a second time. The second line 342 is defined by the pointing location of the Wand 301 at the second point B' and a third point C' at a third time. The pointing locations as determined by the pulse shaped signals are stored in the history for reference. The system 300 can include multiple points for determining alignment and is not limited to a 3-point profile.

As previously indicated the Receiver 302 itself can display alignment information or report the information to remote system to provide visualization. As one example, the LED lights 224 on the Receiver 302 illuminate in accordance with a detected alignment. A single multi-color LED will turn green for perfect alignment (0°), turn yellow if less than 2°, and turn red if alignment is off by 3° or more. With single color LEDS, a varus condition will illuminate the corresponding medial (inside) LED, a valgus condition will illuminate the corresponding lateral (outside) LED, and an alignment less than 1° will show all LEDS green. Other illumination patterns are herein contemplated and are not limited to those described. Similarly, the GUI 307 can report alignment information via text representation of the alignment error or by color coding displayed line segments.

Figure 4:
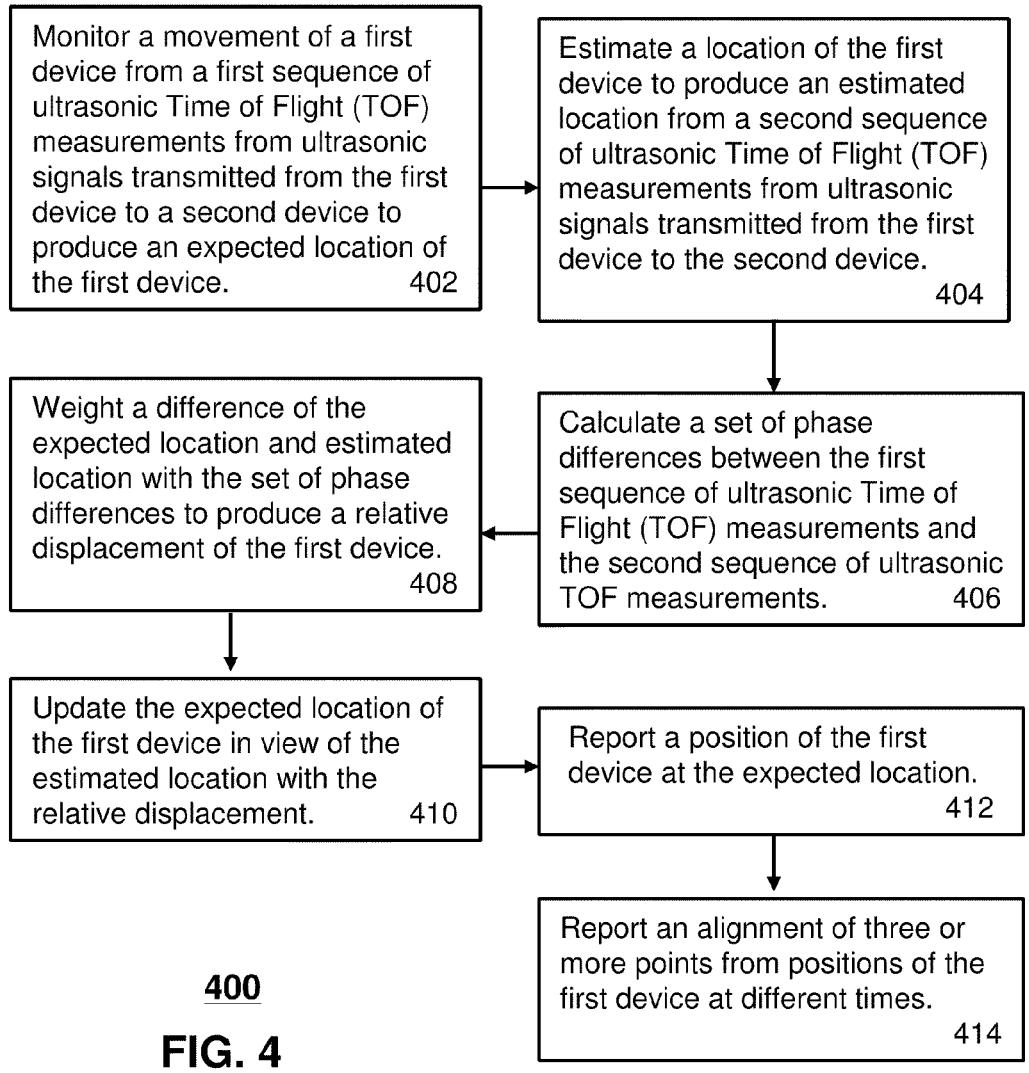
FIG. 4 is a method for resolving movement and position using ultrasonic sensing in accordance with one embodiment.

Referring to FIG. 4 a method 400 for positional measurement is shown. When describing the method 400, reference will be made to FIGS. 2A, 2B and 3A although the method 400 can be practiced in any other suitable system or device. Moreover, the steps of the method 400 are not limited to the particular order in which they are presented in FIG. 4. The inventive method can also have a greater number of steps or a fewer number of steps than those shown in FIG. 3.

At step 402, the second device 220 (e.g., Receiver 302) monitors a movement of the first device 200 (e.g., Wand 301) by measuring a first sequence of Time of Flight (TOF) measurements from ultrasonic signals transmitted from the first device 200 to the second device 220. The measurements produce an expected location of the first device 200. The expected location is a location that is expected in view of the TOF measurements.

Three (3) or more transmitters on the first device 220 perform a sequence of transmissions that occur simultaneously, staggered in time (e.g., delayed transmit) or combination thereof. Each transmitter can transmit at a same frequency (e.g., 40 KHz) and at different frequencies (e.g., 40, 64, 80, 120 KHz). Different fundamental frequency transmit timing patterns can be based on predetermined interference patterns—due to constructive and deconstructive interference of the ultrasonic energy waves. Accordingly, the transmit duration (amount of time the transmitter is vibrating) can be set as a function of the frequencies and timing sequence. Given the speed of sound at 343 m/s, the TOF measurement establishes the distance from each transmitter on the first device 200 to the corresponding receiver on the second device 220 during the movement.

With regard to the components of FIG. 2A, the transmitter 201 receives from the controller 214 a driver signal that describes the transmit shape to be transmitted. As one example the shape can be a square wave that causes a transducer of the transmitter 201 to resonate. In another arrangement, the driver signal can be a frequency modulated or amplitude modulated driver signal provided by the controller 214. One example of pulse shaping is taught in U.S. Pat. No. 7,414,705 entitled "Method and System for Range Measurement" the entire contents of which are hereby incorporated by reference. Alternatively, timing information provided to the controller 214 from the Receiver 302 can include pulse shape information or pulse shape parameters in real-time; that is, the second device 220 directs the first device 200 to transmit ultrasonic pulse signals with a specified shape and at a specified time. The shaping comprises generating an amplitude modulated region, frequency modulated region, constant frequency region, phase modulated region, a chirp region, or a combination thereof.

Returning back to FIG. 4, at step 404, the receiver 220 estimates a location of the first device 200 to produce an estimated location from a second sequence of ultrasonic Time of Flight (TOF) measurements from ultrasonic signals transmitted from the first device to the second device. The estimated location is a point in three-dimensional (3D) space (e.g., <x,y,z>); it can be determined when there is no movement of the first device 200. The second sequence corresponds to simultaneous or staggered-in-time ultrasonic transmissions. The first device 200 can modify (adjust) the sequence pattern as a function of the movement detected by the accelerometer, for example, when it is accelerating, decelerating or when it is held still. The time of flight is a round trip time, that accounting for processing delays, is calculated between when an ultrasonic signal is transmitted from the first device 200 to when it is received (arrives) at the second device 220. Threshold and logic gates in hardware and software can determine when it is received (detected).

One example of detecting arrival time is taught in U.S. patent application Ser. No. 11/562,404 entitled "Method and System for Object Control" the entire contents of which are hereby incorporated by reference. This can include calculating a first Time of Flight of a first pulse shaped signal emitted at a first time from a first transmitter on the first device and received on a first microphone on the second device, calculating a second Time of Flight of a first pulse shaped signal emitted at a second time from a second transmitter on the first device and received on a second microphone on the second device, and calculating a third Time of Flight of a first pulse shaped signal emitted at a third time from a third transmitter on the first device and received on a third microphone on the second device. That is, a time of flight is calculated at each microphone based on the transmitting of only one ultrasonic pulse shaped waveform. For instance, Tx 201 transmits and Rx 221-223 all determine a corresponding TOF; then, Tx 202 transmits and all Rxs listen, and so on.

In a first arrangement, the second device 220 is wired via a tethered electrical connection (e.g., wire) to the first device 200. That is, the communications port of the first device 200 is physically wired to the communications interface of the second device 220 for receiving timing information. The timing information from the second device 220 tells the first device 200 when to transmit and includes optional parameters that can be applied to the ultrasonic signal for pulse shaping. The processor on the second device 220 employs this timing information to establish the first, second and third Time of Flight measurements with respect to a reference time base.

In a second arrangement, the second device 220 is communicatively coupled to the first device 200 via a wireless signaling connection. As previously indicated an infrared transmitter on the first device 200 can transmit an infrared timing signal with each transmitted pulse shaped signal. The Receiver 302 can include a photo diode for determining when the infrared timing signal is received. In this case the communications port of the first device 200 is wirelessly coupled to the communications interface of the second device 220 by way of the infrared transmitter and the photo diode for relaying the timing information to within 3 microsecond accuracy (~1 mm resolution). The processor on the second device 220 employs this infrared timing information to establish the first, second and third Time of Flight measurements with respect to a reference transmit time.

At step 406, the receiver 220 calculates a set of phase differences between the first sequence of ultrasonic Time of Flight (TOF) measurements and the second sequence of ultrasonic Time of Flight (TOF) measurements. A phase difference for each transmit-receiver pair is calculated for the set of phase differences. Phase differences are illustrated and discussed in FIG. 9 of the parent patent application. As one example, there are three phase differences for the ultrasonic signals sent from the transmitters 201-203 of the first device 200 to the receivers 221-223 of the second device 220. The phase difference is a time difference between a first received ultrasonic signal and a second received ultrasonic signal at the same transmitter with respect to a phase of the first received ultrasonic signal.

One example of detecting phase differences is taught in U.S. patent application Ser. No. 11/146,445 the entire contents of which are hereby incorporated by reference. The method step of detecting phase differences can further include calculating a first phase differential between a first transmitted ultrasonic signal and a previously received ultrasonic signal both captured at the first microphone, calculating a second phase differential between the first ultrasonic signal and a previously received ultrasonic signal both captured at the second microphone; and calculating a third phase differential between the first ultrasonic signal and a previously received ultrasonic signal both captured at the third microphone. That is a differential time of flight is calculated for each microphone based on the transmitting of a first ultrasonic waveform and a previously received ultrasonic waveform each at the respective microphone stored in the history.

At step 408, the receiver 220 weights a difference of the expected location and estimated location with the set of phase differences to produce a relative displacement of the first device. One example of applying weighted differences is taught in U.S. patent application Ser. No. 11/562,404 the entire contents of which are hereby incorporated by reference (parent to the immediate application). FIG. 5 of that application illustrates an expected location, an estimated location, and a relative displacement of a first device 200 as determined by a second device 200.

The second device 200 determines the location and movement of the first device 200. In order to track its movement, a history of the first device 200 locations can be stored in the trajectory 430. The trajectory 430 can be a history of expected locations captured over time. An expected location is a weighted average of historic estimated locations that are smoothed over time. The estimated location 436 is a location determined from a direct analysis of the received ultrasonic signals. The trajectory 430 is generally smooth to reflect the continuous movement of the first device 200 relative to the second device 220.

While the first device 200 is moving, it can be expected that its motion will not dramatically depart from the trajectory 430. The object generally moves along a continuum of points. An expected location 432 of the first device 200 can fall within a variance determined from historic locations of the trajectory 430. Accordingly, a next location 432 of the first device 200 can be anticipated to fall within the expected location 432. The next location is also considered the estimated location 436 of the first device 200. The estimated location 436 is a measured position of a current first device 200 location from an analysis of received ultrasonic signals. The estimated 436 location may be accurate or inaccurate.

At step 410, the receiver 220 updates the expected location of the first device with the relative displacement in view of the estimated location. Briefly referring back to FIG. 5 of the parent application Ser. No. 11/562,404 the processor 233 keeps a history of estimated locations 436 and evaluates the history to determine if the estimated location 436 is close to the expected location 432. The relative displacement 438 can be updated based on how close the estimated location 436 is to the expected location 432. In such regard, the first device 200 can be tracked relative to the second device 220 based on relative displacements 438 alone. However, if the relative displacements 438 are imprecise, then over time, the expected location 432 may not match an actual location of the object. That is, the expected location 432 may not coincide with the actual, or absolute, location if the expected location is always updated only on relative displacements 438. Accordingly, the relative displacements 438 are updated to take into account an absolute position of the object by weighting the estimated location 436. However, only an estimate of the absolute position is provided; that is, the estimated location 436.

A phase difference 434 is calculated for the estimated location 436. The phase difference reveals a distance the first device 200 has moved. Accordingly, if the phase difference 434 combined with the estimated location places the first device 200 location outside of the expected location 432, then it can be determined that the estimated location 436 is incorrect. The relative displacement can then be updated based on the expected location 432 alone. If the phase difference combined with the estimated location as determined by the second device 220 places the first device 200 location inside the expected location 432, then it can be determined that the estimated location 436 is correct. The relative displacement can then be updated based on the estimated location 436 and the expected location 432. A weighting can be applied to soft limit the relative displacement updated instead of applying the hard limit. In such regard, the relative displacement can be updated based on a weighting of the estimated location and the expected location.

At step 412, the receiver 220 reports a position of the first device 200 at the expected location. The actual location of the first device 200 is identified by the tip 207, see FIG. 2A. The position of the first device 200 can also describe its orientation. The pointing location of the first device 200 can thus represent the orientation with respect to tip 207 position. To resolve the position, referring to FIG. 2A, the second device 220 converts the time of flight and set of phase difference measurements calculated from each of the received ultrasonic signals at the three microphones 221-223 to three spatial points, and transforms the three spatial points to X, Y and Z rotations around the tip 207. This establishes the orientation of the first device 200. The second device 220 determines the rotations with respect to its local coordinate system (at the origin). The second device 220 thereafter applies a series of translations and rotations to map the first device's 200 coordinate system to its own local coordinate system. This transformation establishes an orientation of the first device 200 and positional location of the tip relative to the second device 220. The mapping includes i) the first device 200 dimensions (e.g., 10×3×10 cm <w,l,h>) and component layout for the local coordinates of the transmitters and the tip 207 that are predetermined, and ii) the second device 220 dimensions (e.g., 6×2×8 cm, <w,l,h>) and component layout for the local coordinates of the microphones and its coordinate origin that are predetermined.

The positional location is where the tip 207 is located in three-dimensional space with respect to an orientation of the first device 200. The positional location can be represented in Cartesian coordinates or polar coordinates. It can be the same point in three-dimensional space even though the wand orientation (e.g., tilt, rotation). The positional location identifies the tip 207 location relative to the second receiver 220 and the spatial coordinates of the three or more transmitters 201-203 relative to the coordinate system of the second receiver 220. It can be reported via sensory feedback, graphical or text display and/or audibly. One example of sensory feedback via ultrasonic sensing and its principles of operation is taught in U.S. patent application Ser. No. 11/562,413 entitled "Method and System for Sensory Feedback" the entire contents of which are hereby incorporated by reference.

At step 412, the receiver 220 reports an alignment of three or more points from positions of the first device at different times. For example, as shown in FIG. 3A, the positional information (e.g., location of the wand tip, orientation) and the alignment can be further rendered to a 3D representation; for example, alignment of the femur and tibia based on resolving the hip center (e.g., femur head location) as previously described and touching the tip 207 of the first device 200 to two more anatomical locations (knee center and ankle center). The GUI 307 displays real-time updates to permit the user to visualize and assess multiple-point alignment. In the example shown, alignment is reported for varus and valgus deviations in accordance with the wand tip positional locations as shown in FIG. 3B.

The illustrations of embodiments described herein are intended to provide a general understanding of the structure of various embodiments, and they are not intended to serve as a complete description of all the elements and features of apparatus and systems that might make use of the structures described herein. Many other embodiments will be apparent to those of skill in the art upon reviewing the above description. Other embodiments may be utilized and derived therefrom, such that structural and logical substitutions and changes may be made without departing from the scope of this disclosure. Figures are also merely representational and may not be drawn to scale. Certain proportions thereof may be exaggerated, while others may be minimized. Accordingly, the specification and drawings are to be regarded in an illustrative rather than a restrictive sense.

Other examples of positional measurement and alignment for orthopedic applications are herein contemplated. As another example a system and method for positioning and inserting a hip cup is provided. The Wand tip can register three locations on the hip to identify a docking target for a hip cup. The Wand 301 can then be affixed to a cup insert instrument to track its orientation relative to the registered docking target. A third example is a system and method for visualizing and reporting vertebral alignment in spine applications. The wand tip can register multiple location on the sacrum to identify a base coordinate system. The wand can then be affixed (or touched) to a vertebra to report alignment relative to the sacrum. The Wand can also be used to trace and report a spine contour for before and after comparison.

Such embodiments of the inventive subject matter may be referred to herein, individually and/or collectively, by the term "invention" merely for convenience and without intending to voluntarily limit the scope of this application to any single invention or inventive concept if more than one is in fact disclosed. Thus, although specific embodiments have been illustrated and described herein, it should be appreciated that any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

The Abstract of the Disclosure is provided to comply with 37 C.F.R. §1.72(b), requiring an abstract that will allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own as a separately claimed subject matter.

What is claimed is:

1. A system for positional measurements, comprising:
an ultrasonic transmitter on a first device for transmitting at a first location a first sequence of ultrasonic signals through air;
a receiver on a second device for capturing the first sequence of ultrasonic signals and a second sequence of ultrasonic signals transmitted by the ultrasonic transmitter on the first device during movement to a second location;
a phase detector on the second device operatively coupled to the receiver for identifying a series of phase differences between the first sequence of ultrasonic signals and the second sequence of ultrasonic signals; and
a processor on the second device operatively coupled to the phase detector and a sensing unit comprising the receiver for updating an expected location of the first device using the series of phase differences, wherein the processor:
measures a first series of Time of Flights (TOF) between the transmitting of the first sequence of ultrasonic signals and the capturing of the second sequence of ultrasonic signals, and producing therefrom the expected location of the first device at the first location,
measures a second series of Time of Flights (TOF) between the transmitting of the first sequence of ultrasonic signals and the capturing of the second sequence of ultrasonic signals, and producing therefrom an estimated location of the first device at the second location,
determines a relative displacement of the first device by weighting a difference of the expected location and estimated location with the phase difference, and
reports a position of the first device in accordance with the relative displacement
wherein the estimated location is determined from the second series of Time of Flight (TOF) measurements, and the relative displacement is evaluated within an error region determined from a series of differential time of flight (dTOF) measurements.

2. The system of claim 1, wherein the processor applies a weighted average to a history of estimated locations for determining the expected location.

3. The method of claim 1, where the processor:
saves to memory three or more location points of the first device at different times; and
reports an alignment of the three or more points of the first device at different times.

4. The system of claim 1, wherein the processor reports an orientation of the first device at the position.

5. The system of claim 1, wherein the processor modifies a timing sequence of the ultrasonic signals transmitted from the first device based on a detected acceleration of the first device.

6. A system for positional measurements, comprising:
an ultrasonic transmitter on a first device for transmitting at a first location a first sequence of ultrasonic signals through air, and
a receiver on a second device for receiving the first sequence of ultrasonic signals and thereafter receiving a second sequence of ultrasonic signals transmitted by the ultrasonic transmitter on the first device;
a phase detector on the second device operatively coupled to the receiver for identifying a series of phase differences between the first sequence of ultrasonic signals and the second sequence of ultrasonic signals; and
a processor operatively coupled to the phase detector and a sensing unit comprising the receiver to:
measure a first series of Time of Flights (TOF) for the first sequence of received ultrasonic signals to produce an expected location of the first device at a first location,
measure a second series of Time of Flights (TOF) for the second sequence of received ultrasonic signals to produce an estimated location of the object at a second location,
apply a weighted difference of the expected location and the estimated location to the phase difference to produce a relative displacement,
update the expected location of the first device with the relative displacement, and
report the expected location of the first device
wherein the processor identifies the estimated location of the first device, and determines if the estimated location is within a region of relative displacement error of the expected location determined from differential time of flight (dTOF) measurements in view of the phase difference.

7. The input device of claim 6, wherein the processor determines the relative displacement of the object in view of the phase difference, the estimated location, and the expected location.

8. The input device of claim 6, wherein the processor
saves to memory three or more location points of the first device at different times; and
reports an alignment of the three or more points of the first device at different times.

9. The input device of claim 6, wherein the processor reports an orientation of the first device at the expected location.

10. A method performed by a processor for resolving movement and position, the method comprising the steps of:
monitoring a movement of a first device from a first sequence of Time of Flight (TOF) measurements from ultrasonic signals transmitted from the first device to a second device that includes the processor to produce an expected location of the first device;
estimating a location of the first device to produce an estimated location from a second sequence of Time of Flight (TOF) measurements from ultrasonic signals transmitted from the first device to the second device;
calculating a set of phase differences between the first sequence of Time of Flight (TOF) measurements and the second sequence of Time of Flight (TOF) measurements;
weighting a difference of the expected location and estimated location with the set of phase differences to produce a relative displacement of the first device;
updating the expected location of the first device in view of the estimated location with the relative displacement; and
reporting a position of the first device at the expected location by
determining if the estimated location is within a region of the relative displacement of the expected location in view of the set of phase differences; and,
if so, updating the expected location with a weighted difference of the estimated location and the relative displacement;
if not, updating the expected location with the relative displacement.

11. The method of claim 10 comprising:
saving to memory three or more location points of the first device at different times; and
reporting an alignment of the three or more points of the first device at different times.

12. The method of claim 10, comprising transmitting a plurality of ultrasonic signals from the first device at staggered time intervals to produce the sequence.

13. The method of claim 10, comprising transmitting a plurality of ultrasonic signals from the first device at a same time to produce the sequence.

14. The method of claim 10, further comprising performing a time weighted average of expected locations for updating the relative displacement.

15. The method of claim 14, further comprising modifying a timing sequence of the ultrasonic signals transmitted from the first device based on a detected acceleration of the first device.

* * * * *